(12) United States Patent
Gilsenan et al.

(10) Patent No.: US 8,938,840 B2
(45) Date of Patent: Jan. 27, 2015

(54) HYGIENIC DOOR HANDLE SYSTEM AND METHOD

(75) Inventors: Daragh Gilsenan, Dublin (IE); John Gleeson, Dublin (IE)

(73) Assignee: Smart Hygiene Ltd., Dublin (IE)

( * ) Notice: Subject to any disclaimer, the term of this patent is extended or adjusted under 35 U.S.C. 154(b) by 296 days.

(21) Appl. No.: 13/387,916

(22) PCT Filed: Jul. 30, 2010

(86) PCT No.: PCT/EP2010/061158
§ 371 (c)(1),
(2), (4) Date: Jan. 30, 2012

(87) PCT Pub. No.: WO2011/012717
PCT Pub. Date: Feb. 3, 2011

(65) Prior Publication Data
US 2012/0131756 A1    May 31, 2012

(30) Foreign Application Priority Data

Jul. 31, 2009 (GB) .................................. 0913395.0

(51) Int. Cl.
*A61L 2/23*    (2006.01)
*E05B 1/00*    (2006.01)
*A61L 2/18*    (2006.01)
(Continued)

(52) U.S. Cl.
CPC ................. *E05B 1/0069* (2013.01); *A61L 2/18* (2013.01); *A61L 2/24* (2013.01); *A61L 2/23* (2013.01); *A61L 2202/15* (2013.01); *E05B 15/002* (2013.01); *Y10S 16/904* (2013.01)
USPC ........................................... 15/103.5; 16/904

(58) Field of Classification Search
CPC ...... Y10S 16/904; E05B 1/0069; A47K 10/34
USPC .................................. 15/103.5; 16/412, 904
See application file for complete search history.

(56) References Cited

U.S. PATENT DOCUMENTS

| 4,046,508 A | 9/1977 | McDonald |
| 4,710,634 A * | 12/1987 | Brookes ................... 250/455.11 |
| 4,997,139 A * | 3/1991 | Menard ......................... 242/535 |

(Continued)

FOREIGN PATENT DOCUMENTS

| DE | 202007004498 U1 | 8/2008 |
| EP | 1164235 A2 | 12/2001 |

(Continued)

OTHER PUBLICATIONS

PCT International Search Report and Written Opinion for International Application No. PCT/EP2010/061158, mailed Dec. 20, 2010, 11 pgs.

*Primary Examiner* — Laura C Guidotti
(74) *Attorney, Agent, or Firm* — K&L Gates LLP

(57) ABSTRACT

The invention provides a system and method for self-cleaning a door handle (4) by utilizing the kinetic energy of opening a door (1). A cable (3), for example a multi-link chain, fixed to the door frame (2) and a gear assembly (10, 11, 12) is provided such that linear displacement of said cable is converted to potential energy in response to movement of said door. The invention provides a means for rotating a drive roller (5) to co-operate with the door handle to clean said door handle, only when the door handle is released and the door is closing or closed. The potential energy provides the energy to enable the rotation of the drive roller.

20 Claims, 14 Drawing Sheets

(51) Int. Cl.
*A61L 2/24* (2006.01)
*E05B 15/00* (2006.01)

(56) References Cited

U.S. PATENT DOCUMENTS

| | | |
|---|---|---|
| 7,080,427 B1 | 7/2006 | Campopiano et al. |
| 7,458,742 B2 * | 12/2008 | Stropkay et al. ............... 401/205 |
| 7,850,114 B2 * | 12/2010 | Lavy ............................. 242/538 |
| 2010/0155409 A1 * | 6/2010 | Muderlak et al. ............... 221/30 |

FOREIGN PATENT DOCUMENTS

| | | | | |
|---|---|---|---|---|
| GB | 2411344 A | * | 8/2005 | ............. A47L 25/08 |
| WO | 2008/035121 A1 | | 3/2008 | |

\* cited by examiner

E-E ( 0.40 : 1 )

HYGIENIC DOOR HANDLE SYSTEM AND METHOD

CROSS REFERENCE TO RELATED APPLICATIONS

This application is a national phase application under 35 U.S.C. §371 of International Application No. PCT/EP2010/061158, filed on Jul. 30, 2010, which claims priority to and the benefit of GB Patent Application No. 0913395.0, filed on Jul. 31, 2009, the entire disclosures of each of which are incorporated by reference herein.

FIELD OF THE INVENTION

The invention relates to a self-cleaning handle for a door. In particular the invention utilises a process of harnessing the kinetic energy of any door being opened, and to utilise the kinetic energy to disinfect an associated door handle.

BACKGROUND TO THE INVENTION

Nosocomial infections or Health Care Associated Infections (HCAIs) are a major financial and safety concern in hospitals and Health Care Service Units (HCSUs) worldwide. HCAIs are defined as infections that result from treatment or care of a patient within a hospital or health care service unit but are secondary to the patient's original presenting condition. The prevalence of these HCAIs has increased dramatically in the last century as a result of a number of significant factors, most notably the emergence of antibiotic or anti-microbial resistant strains of a large range of common microorganisms. Additional factors related to the increased prevalence include consolidation of hospitals/health care service units nationally (resulting in larger numbers of patients housed together, often in an immunocompromised state), increased use of outpatient treatment (consequently people in hospitals are sicker on average as a direct result), the movement of medical staff and personnel from patient to patient acting as vectors for disease transmission, lack of rigid sanitation protocols and/or enforcement, and the over-prescription of antibiotics or anti-microbial drugs.

The prevalence of these nosocomial infections is extremely relevant clinically. In the United States (US), it is estimated that the rate of HCAI prevalence is as high as 10% (or two million patients infected) per annum (p.a.). The proportion of these two million infected patients that result in patient morbidity is about 5% or 100,000 deaths p.a. Encouragingly it is estimated that at least one third of all nosocomial infections are preventable with the effective application of sufficient disinfection precautions. In Europe, the morbidity rate is very similar with prevalence rates of approximately 7% in France, 7% in Italy, 7.6% in England, 8.2% in Wales and 5.5% in Northern Ireland. The Republic of Ireland has the lowest prevalence rate of 4.9%. Annual estimated costs for HCAIs run as high as $11 billion in the US (approx 0.1% of US GDP) and £1 billion in the UK (approx 0.05% of UK GDP) with a potential avoidable cost of at least £150 million p.a. in the UK alone.

There are many infectious diseases associated with hospital and HCSUs. Several routes of transmission are commonly available in all these settings, specifically (i) contact, (ii) droplet, (iii) airborne and (iv) common vehicle transmission. High touch surfaces such as door handles, door knobs etc. are extremely effective reservoirs for contact-transmitted infections and can support a large number of different strains of infectious microorganisms. These contact-transmitted infections include *Acinetobacter* (pneumonia), *Burkholderia cepacia* (respiratory infections), Clostridium Difficile (intestinal infections, diarrhoea), *Colstridium Sordelli* (nausea, vomiting), Viral Haemorrhagic Fever, gastrointestinal infections, Hepatitis-A (liver disease), Methicillin-resistant *Staphylococcus Aureus* (MRSA), Parvovirus, and Severe Acute Respiratory Syndrome (SARS). Although immunocompromised patients are most at risk, HCAI microorganisms are widespread and carried on a large proportion of the population's skin with significant morbidity in non-immunosuppressed patients. Worryingly, prevalence rates are largely underestimated as currently data is only collected in the more serious cases of HCAI. MRSA is the best known of all these contact-transmitted HCAIs, with 10% of all HCAIs being attributed to MRSA alone and approximately 33% of the population carrying MRSA. Previous scientific studies have shown worrying evidence of high-touch surface contamination within hospitals and HCSUs. *Staphylococcus Aureus* identified on approximately 30% of all room door handles, suggesting extensive contamination within these environments. Consequently, MRSA is almost universally used as the benchmark for all qualitative and quantitative measures of HCAI prevalence and curative efficacy.

Successful preventative and curative measures in the past have targeted several routes of transmission to counteract the rapid spread of HCAIs. Traditionally, these measures have focussed on the most obvious route of infection, namely through direct contact transmission (e.g. body surface to body surface, hand contact between source and prospective host). The promotion of hand washing is frequently seen as the single most important measure currently employed to reduce risk of infection, with the adoption of alcohol-based hand gels being recommended as the primary means of hand hygiene in Irish, Centre for Disease Control (CDC) and World Health Organisation (WHO) published guidelines. Measurement of the consumption of alcohol-based hand gels, expressed as volume per bed days, has been shown to correlate with overall hand hygiene activity within hospitals. However, current data collection methods are significantly flawed and the resulting conclusions drawn from these reports, regarding the efficacy of this method, are tenuous. The method of data collection commonly quantifies the volume of hand gel consumed, with no measure of gel wastage or premature replacement of gel containers before their contents are completely exhausted. Additionally, data does not distinguish between patient, visitor or health care worker consumption within the surveyed location.

Concurrently, this approach to disease transmission prevention has a number of significant additional disadvantages, specifically associated with the human compliance required to ensure its effectiveness. Firstly, this method of transmission prevention and its efficacy are entirely dependent on the individuals due diligence in utilising this method of infection prevention with sufficient frequency. This is further compounded by the necessity to comply both before and after any and all contact with potentially infectious sources, such as patients or hospital/health care service unit equipment. Given the numerous factors that influence this aspect (e.g. patient behaviour/belief system, hospital/health care service unit culture, product availability, location of product dispensers/applicators, hand washing technique etc.), this method of infection transmission prevention is effective when utilised but far from exhaustive. Recent studies have shown that there is still a significant variation in the alcohol-based gel consumption from hospital to hospital nationwide. Worryingly, additional studies looking at consultant compliance reported that consistently low hand washing rates were observed, in spite of special education programmes and subsequently monitored evaluation of consultant technique and hand washing compliance. An ideal solution to the problem would serve to remove the element of user compliance and ensure a mandatory but unobtrusive method of disinfection of the users hand and/or the associated equipment surface.

Secondly, this method of transmission is only one method by which HCAIs are spread throughout hospitals and HCSUs. Indirect contact and common vehicle transmission are rarely implicated in disease transmission, despite the fact that the surrounding environment acts as a reservoir for a multitude of infectious micro-organisms. Inadvertent exposure to such environmental opportunistic pathogens may result in infections with significant morbidity and/or mortality. The environmental reservoir can act as a very efficient way for micro-organisms to spread, with enterococci as an example. This micro-organism can persist on a dry environmental surface in a viable infectious state for up to seven days, with some environments supporting survival for as long as four months after initial contamination.

Thirdly, transmission of micro-organisms from environmental surfaces to patients is largely via hand contact with the surface in question. Although it is well accepted that hand hygiene is a vital component in the HCAI transmission cycle, environmental disinfection is rarely promoted amongst the general population. This is especially worrying given the high levels of patient, visitor and staff mobility and interaction within typical specialist Hospitals and HCSUs worldwide. In fact it can be argued that it is the public population, not the staff that pose the highest risk regarding the introduction of pathogens into the hospital/HCSU setting.

Finally, one of the biggest dangers relating to contamination of environmental surfaces is the efficacy of alcohol-based hand gels. It has been long accepted by the U.S. Food and Drug Administration (FDA) that germicidal chemicals, approved by the FDA as skin antiseptics (such as alcohol-based gels), are completely inappropriate for use as environmental surface disinfectants. This serves to highlight the vital role that regular environmental disinfection plays in the HCAI transmission cycle. Specialist units within Hospitals (such as burns units) are particularly susceptible to HCAIs found on environmental surfaces, given that dermally-compromised patients are missing the bodies most fundamental form of protection against micro-organisms, namely skin.

Contaminated hands have been shown to be extremely effective vectors for disease transmission both from and to inanimate equipment, specifically being capable of supporting micro-organism transfer to additional surfaces. Given the average rate of hand hygiene compliance of approximately 50%, the transiently contaminated hand of an average health care worker (contaminated by an inanimate object) becomes a major route of transmission. This highlights the significant problem with the primary reliance on hand hygiene as the major preventative measure against HCAIs. Hand hygiene alone is not effective if the environment itself is heavily contaminated. The problem with hand washing is that it is impossible to get everyone to do it at the most appropriate and effective time.

High touch surfaces (such as door handles, door knobs etc.) need to be cleaned regularly given the high daily touch rate, and consequently potential for HCAI transmission, of these surfaces within a Health Care setting. There have been a significant number of scientific studies that have been conducted that provide significant evidence of the role the inanimate environment plays in the transmission cycle. This has lead to the widespread acceptance of the importance of environmental cleaning, especially in the control of nosocomial outbreaks. In spite of this widespread acknowledgment, priority is typically given to the cleaning and disinfection of floors and toilet areas. A number of devices have been proposed to provide self cleaning door handles or door knobs.

One device that attempts to solve the problem of cleaning door handles regularly is disclosed in U.S. Pat. No. 4,046, 508, issued to McDonald. The McDonald patent discloses a self-cleaning door handle apparatus that is intended to be mechanically operated when the door is opened. As can be seen in the figures and described in the specification, it is intended that a rod is to be pushed by the opening of the door, which causes a pawl to engage a gear to turn a wheel, which functions as the door handle. As the wheel turns, it passes through a wipe that applies a sterile solution to the wheel from a reservoir. The apparatus also has a squeegee to dry the surface of the wheel. A critical flaw in this invention, however, is the fact that the wheel turns as the user operates the door. This is precisely when the device should not operate because the user is grasping the wheel. Moreover, the inherent design of using the push rod will not function as anticipated and makes the device prone to jamming. In particular, the travel distance between the door and the door jamb is insufficient to push the rod a sufficient distance to drive the wheel. Therefore, there is a need of a self-cleaning door handle device that does not operate while the user is grasping he handle and a self-cleaning door handle device that functions properly and is less prone to jamming.

Another U.S. Pat. No. 7,080,427, Campopiano, discloses a self-cleaning handle for a self-closing door. The door is movable by a user between a normally closed position and an open position, and is automatically moved from the open position back to the closed position. The handle having a housing secured to said door and a handle rotatably mounted in the housing. An unexposed portion of the handle is disposed within the housing and an exposed portion of the handle is exposed for grasping by a user to open the door. A cleaning wipe is disposed within the housing and is slidably engaged with the unexposed portion of said handle. This patent asserts that the gap between the body of an open door and its associated door jam is insufficient to drive a door handle self-sterilising device. This patent does not include a method of preventing damage to the device if the door handle is not allowed to operate during door closing and is subsequently driven by repetitive door opening and closing cycles. This is a serious flaw in the design of this patent. This device does not appear to have a safety system, preventing the device from operation if the user holds the handle while the door closes and the device tries to operate. This is a major safety flaw. This patent describes a direct-drive device that would not work on doors that swing both ways, such as those found in hospitals or HCSUs.

There is therefore a need to provide a device system and method to sterilise/disinfect a surface effectively and prevent the transmission of diseases in an environment, for example a hospital, which overcomes the above mentioned problems.

SUMMARY OF THE INVENTION

According to the present invention there is provided, as set out in the appended claims, a system for self-cleaning a door handle by utilising the kinetic energy of opening a door, comprising:

a cable, for example a multi-link chain, fixed to a door frame and a transmission assembly such that linear displacement of said cable is converted to potential energy in response to movement of said door;

means for rotating a drive roller to co-operate with the door handle to rotate and to clean said door handle, only when the door handle is released and the door is closing or closed.

The invention completely eradicates one of the major routes of microorganism transmission by automatically and unobtrusively disinfecting door high touch surfaces every time the door is used. In addition this invention also facilitates the scheduling of disinfection at predetermined and computer-controlled intervals. The invention uses only notionally-free energy, applied by the door user when opening the door as normal, to power the device. Consequently, the invention acts as a barrier to a common infection route through one of the most frequently touched surfaces within a hospital or HCSU, namely the door handles. The means for rotating is adapted such that the device operation only occurs when the external interfaces (i.e. handle of the door) are released. Conversely, the application of force or torque to the external interfaces will halt movement of the interfaces, ensuring safe and ergonomic operation of the device at all times.

In one embodiment the means for rotating comprises a worm gear and a spur gear, wherein the worm gear cooperates with a shaft, such that the shaft rotates only when the door handle is released and the door is closing. The application of a worm and spur gear drive train ensures that the door handle/pad cannot be moved/rotated by the user and the application of force/torque to the external interfaces.

In one embodiment the worm gear teeth engage with the spur gear and mounted coaxially with one of a driving roller mounting shaft to rotated said drive roller.

In one embodiment a mechanism, for example a ratchet mechanism, coupled to the worm gear allows independent movement or rotation of the shaft ends, such that the mechanism only allows rotation in one direction.

In one embodiment, device rotation will be halted independent of the worm/spur gear drive train by the application of a friction braking mechanism. This braking mechanism may be mechanically or electronically applied when the user applies a force at the door handle.

In one embodiment the means for rotating comprises a differential transmission engaged with the drive train.

In one embodiment the means for rotating comprises a system of pulleys connecting the energy storing device to the drive train.

In one embodiment the means for rotating comprises a rack and pinion system connecting the energy storing device to the drive train.

In one embodiment the means for rotating comprises a system of clockwork style clutches and cams.

In one embodiment the means for rotating comprises a bevel gear transmission.

In one embodiment the means for rotating comprises a helical gear transmission.

In one embodiment the cable is connected to the means for rotating and the door frame through a channel bored through the door.

In one embodiment the cable is connected to the means for rotating and the door frame through a conduit positioned along the surface of the door or embedded in the door.

In one embodiment the required quantity of potential energy for the means for rotation is generated after said door opens through an angle of 30 degrees or greater about the door rotational axis with respect to the door frame.

In another embodiment, the door handle is fixed in a horizontal orientation at a fixed mounting point at one end adapted to allow a relative amount of displacement at the opposite end, facilitating angular displacement of the handle about the fixed mounting point, wherein said angular displacement generates potential energy to facilitate rotation of the door handle to clean said handle.

In one embodiment the device is orientated to facilitate the application of a turning force or moment to the door handle.

In one embodiment a door latching mechanism is operated when the user applies a torque to the door handle.

In one embodiment the required quantity of potential energy for the means for rotation is generated by the rotation of the door handle about a fixed mounting point as the user applies a moment to the handle to unlatch the door.

In one embodiment potential energy stored is used to rotate the door handle at least through 180 degrees of rotation.

The potential energy generated is preferably stored using a potential energy storage mechanism, for example a spring coil, spiral spring, tension spring, torsion spring or extension spring mechanism. A slip clutch can be located between the coil spring mechanism and a fixed shaft mounting point to ensure that the coil spring to prevent excessive coiling/tightening of the coil spring mechanism. The coil spring can be pre-tensioned using a restrictive collar to ensure efficient and complete operation of the system.

In one embodiment, a differential transmission can be used to dissipate the energy stored in the energy storage device.

In a further embodiment of the present invention there is provided a cartridge for storing disinfectant liquid. The cartridge is adapted to cooperate with said drive roller to supply disinfectant liquid to clean said door handle.

In one embodiment the cartridge comprises a spring based element to apply a force on said liquid to ensure optimum supply of liquid to said drive roller.

In one embodiment the liquid in the cartridge is applied to the handle by means of a gravity fed applicator.

In one embodiment the cartridge comprises a visible indicator to indicate the amount of disinfectant liquid stored in said cartridge.

In another embodiment of the present invention there is provided a system for self-cleaning a door handle, said system comprising:
　a power supply; and
　means for rotating a drive roller using said power supply to co-operate with the door handle to rotate and to clean said door handle, only when the door handle is released and the door is closing.

In a further embodiment of the present invention there is provided a system for self-cleaning a door handle by utilising the kinetic energy of opening a door, comprising:
　means for storing potential energy in response to movement of said door; and
　means for rotating a drive roller to co-operate with the door handle to rotate and to clean said door handle, only when the door handle is released and the door is closing.

In a further embodiment of the present invention there is provided a system for self-cleaning a door handle, wherein the door handle is fixed to a door panel at a fixed mounting point at one end and adapted to allow a relative amount of displacement at the opposite end, facilitating angular displacement of the handle about the fixed mounting point, wherein said angular displacement generates potential energy to facilitate rotation of the door handle to clean said handle.

BRIEF DESCRIPTION OF THE DRAWINGS

The invention will be more clearly understood from the following description of an embodiment thereof, given by way of example only, with reference to the accompanying drawings, in which:—

FIG. 7 illustrates a schematic illustrating an enlarged view of the worm gear drive mechanism within the device of FIG. 3a;

DETAILED DESCRIPTION OF THE DRAWINGS

Figure 1:
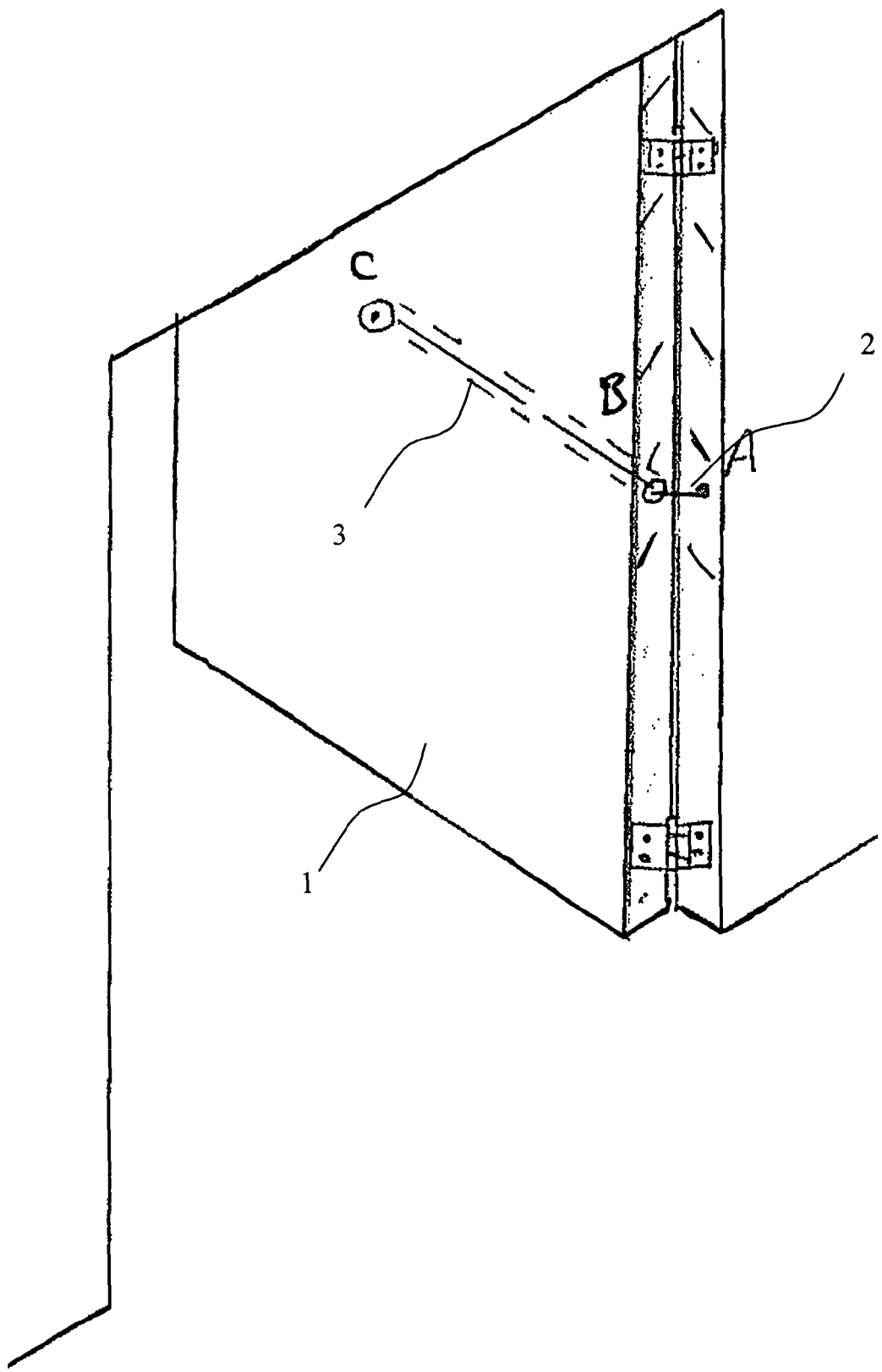
FIG. 1 illustrates a schematic illustrating the preferred method of sterilisation motor.
Figure 2:
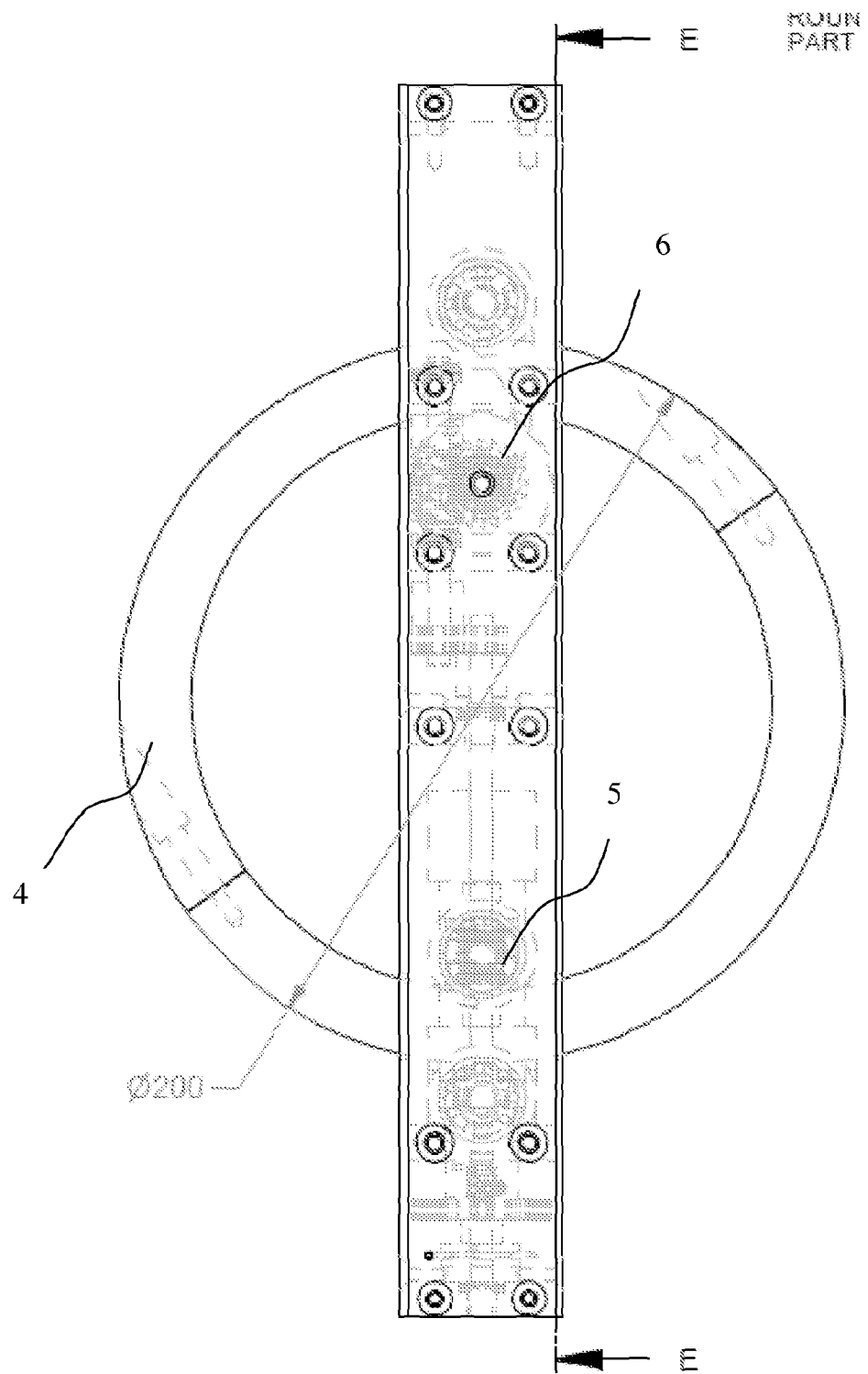
FIG. 2 illustrates a schematic illustrating elevation view of the circular door handle and associated drive/roller system.
Figure 2A:
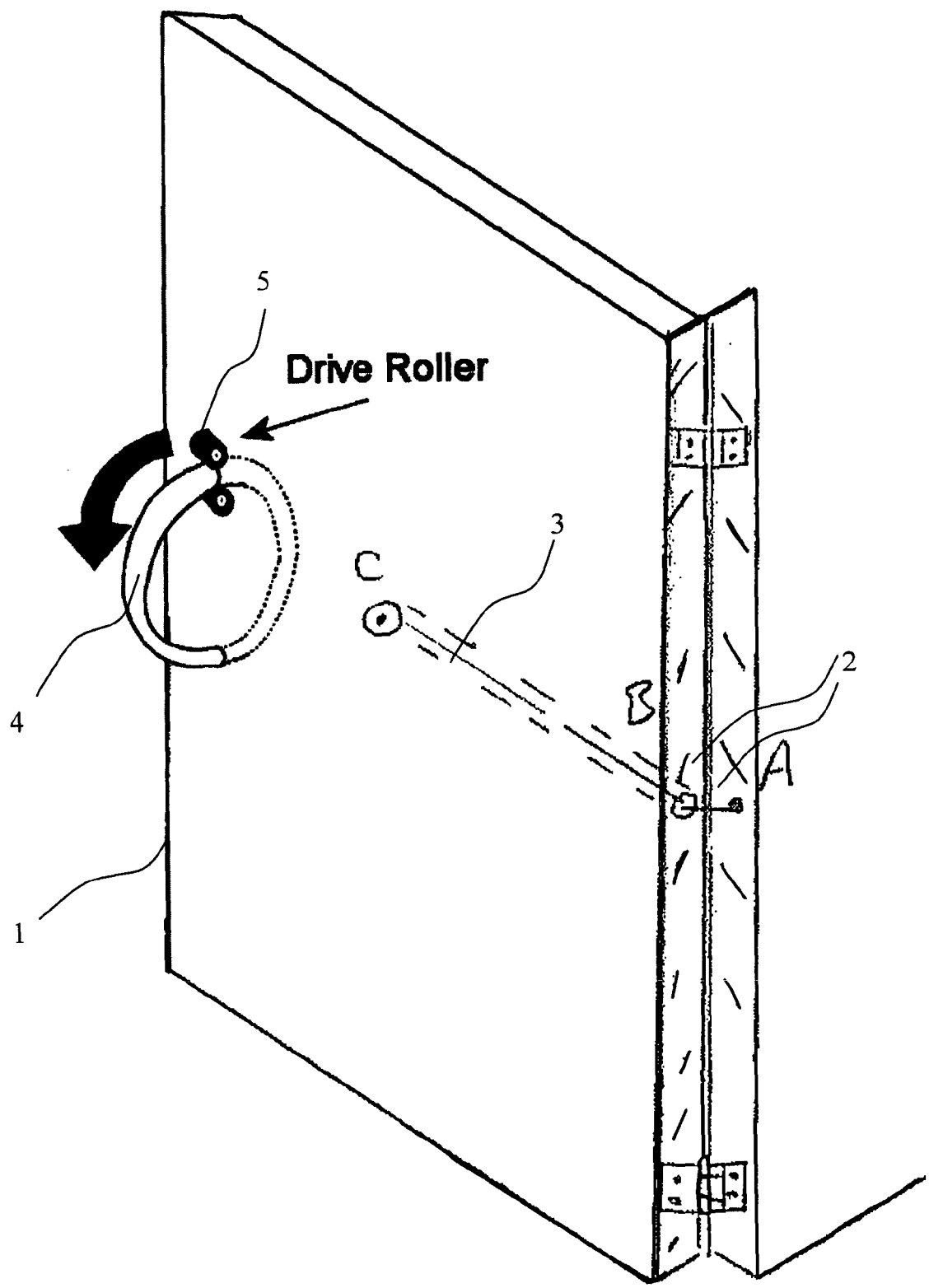
FIG. 2a illustrates a schematic illustrating the layout of the circular door handle and one pair of associated rollers.
Figure 3:
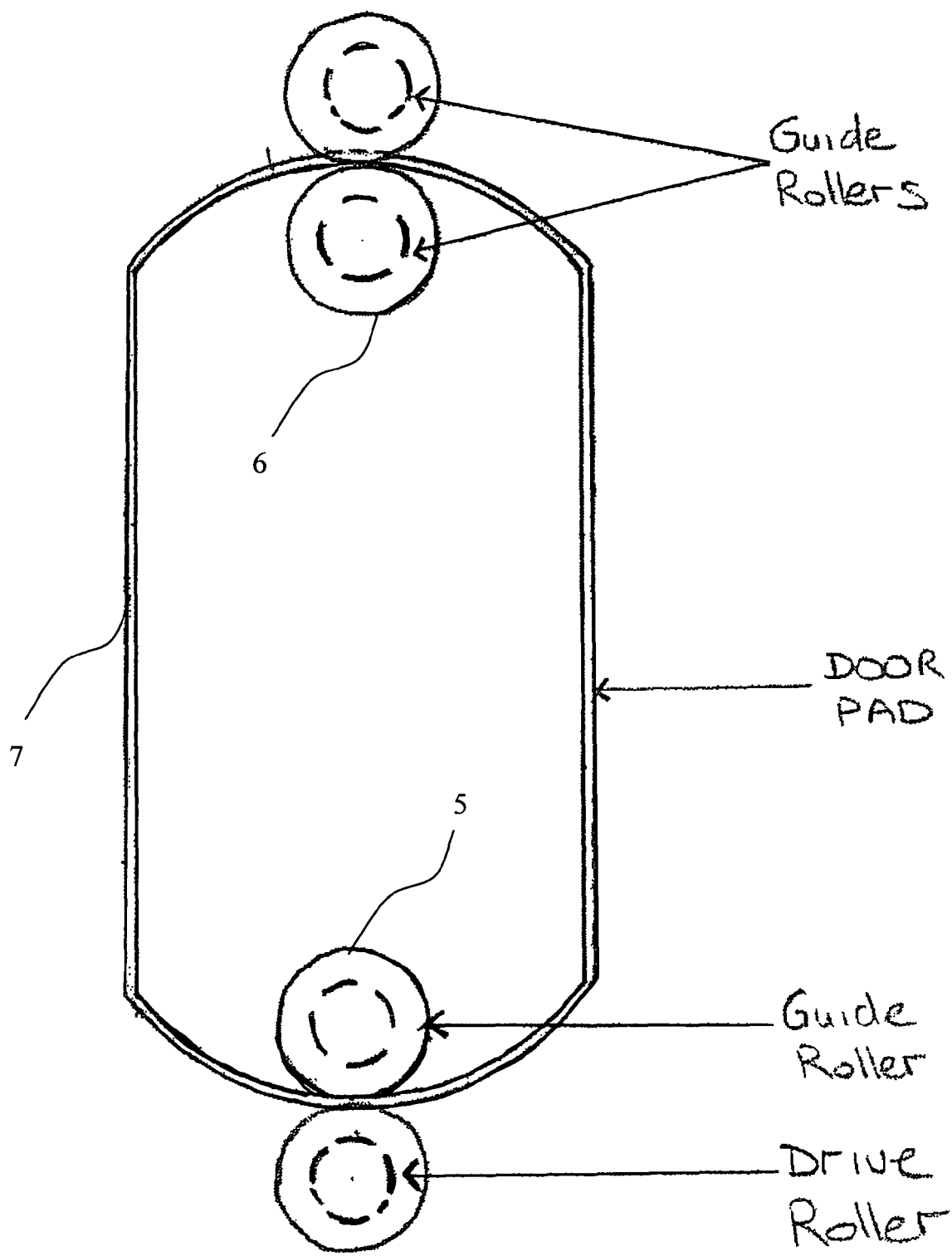
FIG. 3 illustrates a schematic illustrating elevation view of the door handle pad and associated drive/roller system.
Figure 3A:
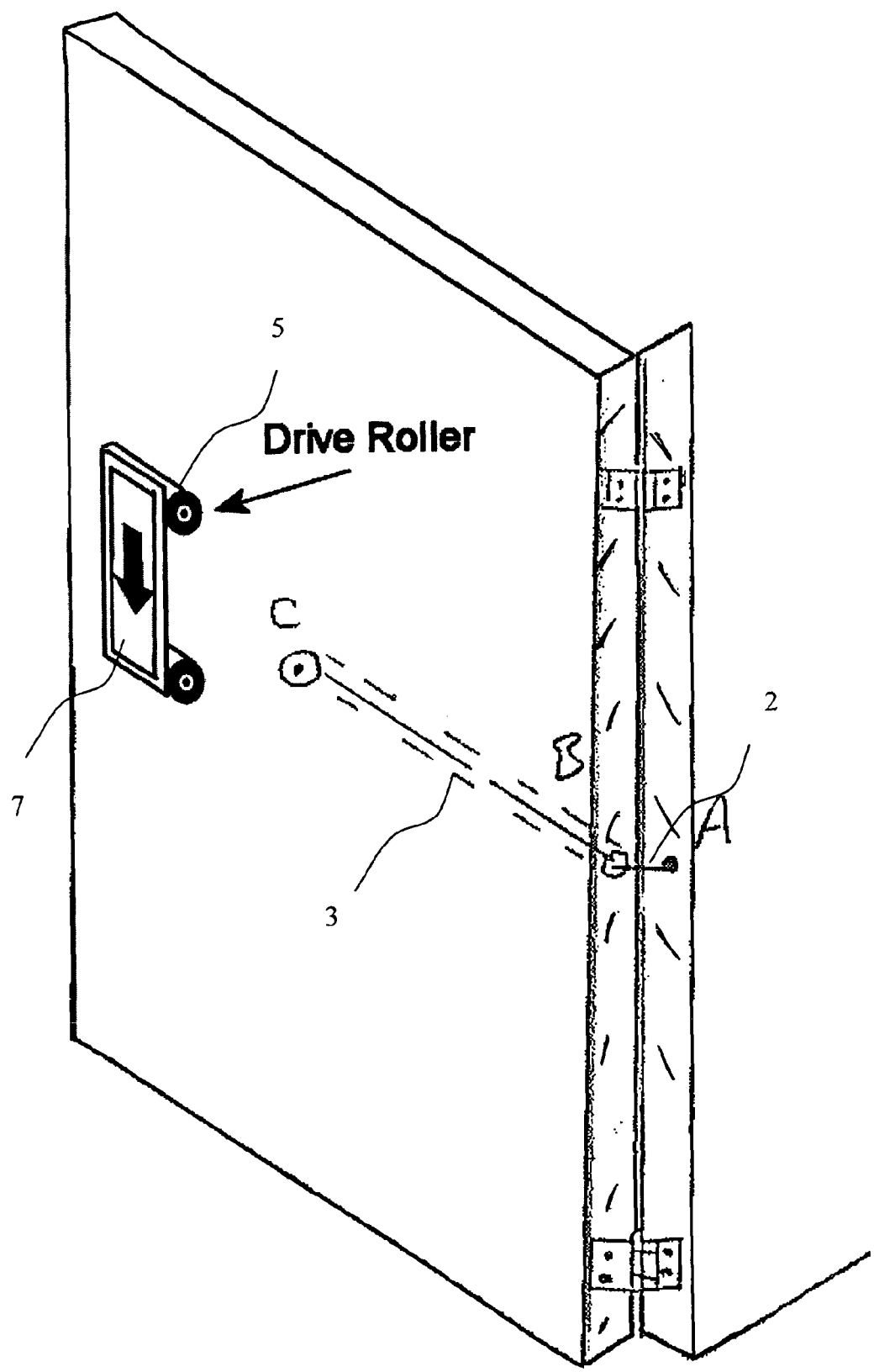
FIG. 3a illustrates a schematic illustrating the layout of the door handle pad and one pair of associated rollers.

Referring to FIG. 1 illustrates a system designed to harness the kinetic energy, imparted to a door (1) opened by an individual, to power an in situ handle sterilisation machine. The device is activated or "charged" when an applied force opens the door about its fixed axis of rotation. The kinetic energy is harnessed by using the displacement that occurs between the inner edge of the door (1) and a door jamb (2), as illustrated in FIG. 1. This displacement is harnessed by attaching a non-elastic but flexible cord (3) (e.g. a multi-link chain) at a fixed point in the door jamb (2). The cord (3) is connected to motor within the device enclosure through a channel bored through the door. The device motor converts this kinetic energy into a stored potential energy to subsequently drive the device. This aspect of the design ensures that the invention can be utilised on any door, irrespective of the direction of swing.

The device is designed to store the required quantity of energy for operation after a door opening angle of 30 degrees or greater about the door rotational axis. This angle can be infinitely adjusted within the range of 1 degree up to 90 degrees rotation about the door axis by adjusting the device gear ratios within the device gearbox. The device is consequently primed for operation. The device will only activate once the door is released and the handle is free to rotate. This is a specific and inventive aspect of this invention made possible by the use of a worm/spur gear drive train. As the door closes, the potential energy stored is used to rotate the door handle/pad through 180 degrees of rotation. This drives the door handle/pad past/through the disinfectant applicators/reservoir located at both the top and bottom of the device enclosure interior, resulting in a homogenously disinfected door handle/pad surface. The device is designed to permit device operation only when the user is no longer in contact with the handle.

The system of the present invention consists of three main components which will be described in detail, namely the door handle sterilisation machine enclosure, the door handle sterilisation machine, and the door handle sterilisation motor. The door handle sterilisation machine enclosure is a hollow, protective cover that contains the door handle sterilisation motor, four circular or rectangular apertures to facilitate the insertion and movement of the circular door handle or optional alternative, a sterilised door pad. The enclosure will consist of two sides, one slightly smaller in cross-sectional area than the other, facilitating the insertion of one side into the other and allowing the customisable width of the unit to retro fit a range of door of variable width.

The door handle sterilisation machine consists of an external surface (that is automatically cleaned only when the user is no longer in contact with the external surface), a disinfectant reservoir located internally within the device enclosure, and an interface mechanism facilitating the sterilisation of the external user surface as the device is driven by the door handle sterilisation motor. This mechanism can include physical immersion in the disinfectant media and/or a gravity of pressure fed system which would apply the disinfectant through physical contact, such as an interfacial coating surface. This surface can be flexible or rigid and can be manufactured using a number of different material types selected from any material or combination of materials selected from the following list; metals, polymers or ceramics.

Figure 4:
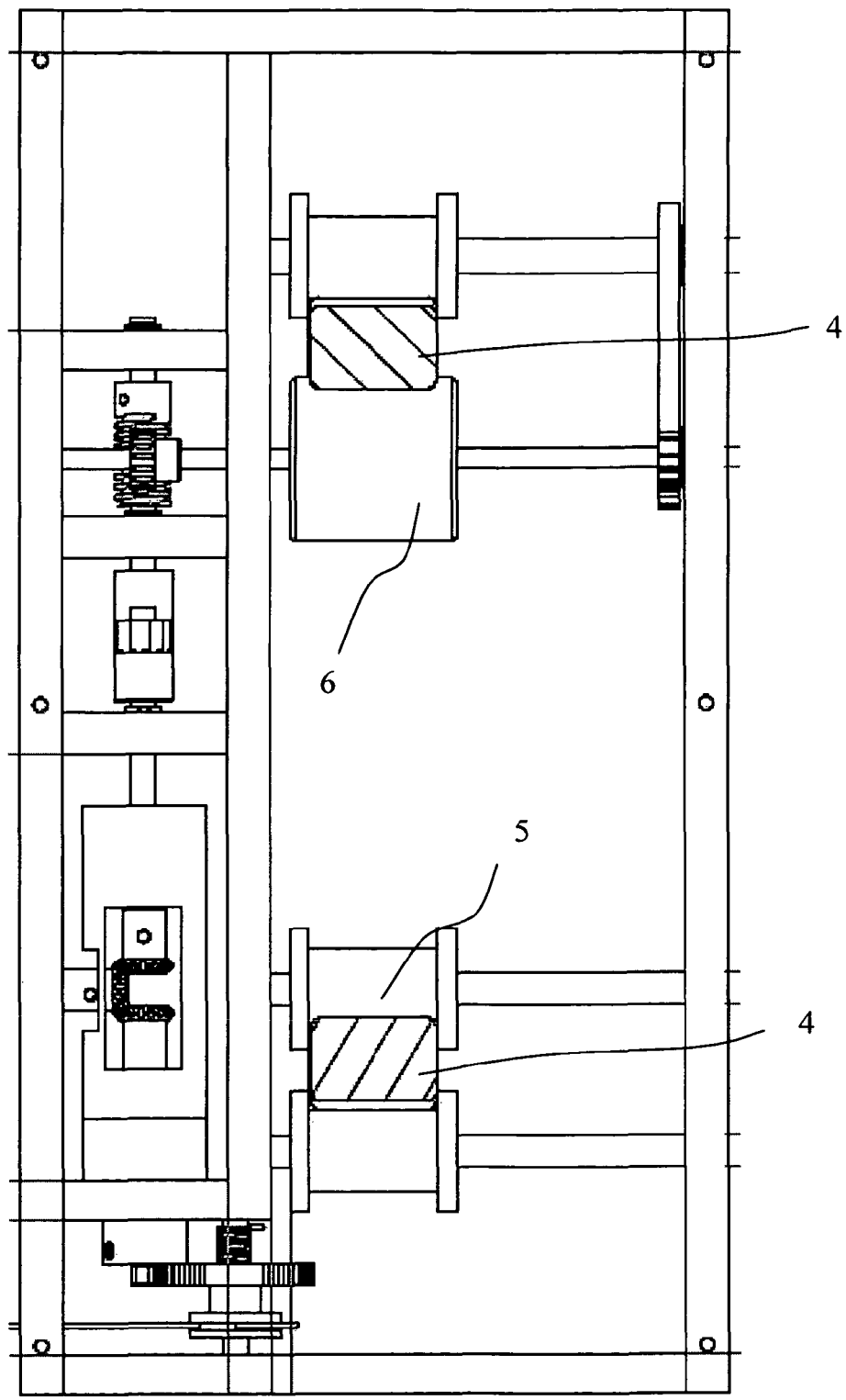
FIG. 4 illustrates a schematic illustrating the in-plane elevation of the circular door handle and the concave contour of a preferred roller embodiment.

External Interface:

The door handle sterilisation machine external surface can take the form of a circular door handle, a latched door handle or a push pad, capable of rotation about their diametric or orthogonal centres respectively, as illustrated by FIGS. 2, 2a, 2b, 3 and 3a. The circular door handle (4), or alternatively the door pad (7), can be held in place by four rollers in total, two at the top (6) of the device and two at the bottom (5). In the case of both the circular door handle (4) and the door pad (7), the rollers act as physical supports and preferably, but not necessarily, drive surfaces simultaneously. One set of the rollers (6) can be adjusted vertically to facilitate correct setting of the door pad material tension, using a slot cut in the door handle sterilisation machine enclosure. The circular door handle (4) is preferably circular in cross-section, as illustrated by FIG. 4, and can be manufactured using any material or combination of materials from the following: metal, polymer or ceramic. Preferably, the material surface finish is smooth and free of defects that would act as local reservoirs for microorganisms. Preferably the material is matched with the in situ supporting and driving rollers (5) to ensure a high friction interface between both moving surfaces.

The door pad (7) is preferably rectangular in cross-section and can be of any functional thickness. Preferably the door pad material is made from any flexible material or fabric. The door pad (7) motion can be driven by rollers or an alternative mechanism of drive known to a person skilled in the art. Preferably, in the case of a friction drive mechanism, the door pad material should be made from a material from the previous group that is matched with the roller material to ensure a high friction contact when the rollers act as door pad movement drivers. Alternatively, if the material is driven by other means, it would preferably be made from any flexible material or fabric. The rollers can act as supports and/or door pad material tensioning devices simultaneously.

In the case of the circular door handle, the supporting and driving rollers are circular about their axis of rotation but are preferably, but not necessarily, convex in the direction of door handle rotation, as illustrated by FIG. 4, conforming to the curvature of the in situ door handle. In the case of the door pad, the supporting rollers act as drivers and tensioners for the pad material. The rollers are circular about their axis of rotation but are preferably, but not necessarily, flat in the direction of door pad travel. The roller material can be made from any material or combination of materials from the following list; metal, polymer or ceramic. Preferably the roller surface material can be manufactured from a material matched with the in situ rotating circular door handle/door pad to ensure a high friction contact between the two surfaces.

Disinfectant Reservoir:

The disinfectant reservoir can be located within the door handle sterilisation machine enclosure and is comprised of a non-porous vessel of fixed volume, containing an inlet port for device filling and refilling with a suitable disinfectant, and outlet port to facilitate application of the disinfectant to the external surface (namely the door handle or the door pad). An observation port to facilitate visual inspection and measurement of reservoir fluid level without the need for device disassembly is preferable. The disinfectant reservoir can be made from any material or combination of materials from the following list; metal, polymer or ceramic. Preferably, the reservoir can be made from a chemically inert material to ensure longevity and normal function of the device. Preferably, the reservoir can be made from a range of materials specifically chemically inert with respect to the preferable disinfectant contained within the reservoir.

The disinfectant material contained within the reservoir can be composed of one of, or any combination of, the following forms of matter: solid, liquid or gas. The disinfectant material can be expelled from the reservoir using any existing method of matter expulsion known to someone skilled in the art. Preferably, the disinfectant is expelled from the reservoir using mechanical force or pressure. Preferably, the disinfectant is expelled using a gravity-fed system, utilising the notionally free gravitational force available. Alternatively, the disinfectant can be expelled using mechanical, hydraulic or pneumatic pressure. Alternatively, the disinfectant can be expelled using diffusion through a porous medium. The disinfectant material can be applied to the moving surfaces of the door handle or the door pad using a number of different methods. The disinfectant is applied using any one of, or any combination of, the following methods; physical contact, fluid flow or aspiration using any of the methods outlined within this paragraph. The disinfectant material and the door handle/door pad can be connected directly or remotely using any number of methods known to a person skilled in the art (e.g. tubing, pipe work etc.).

Example Operation of the Invention

Figure 5:
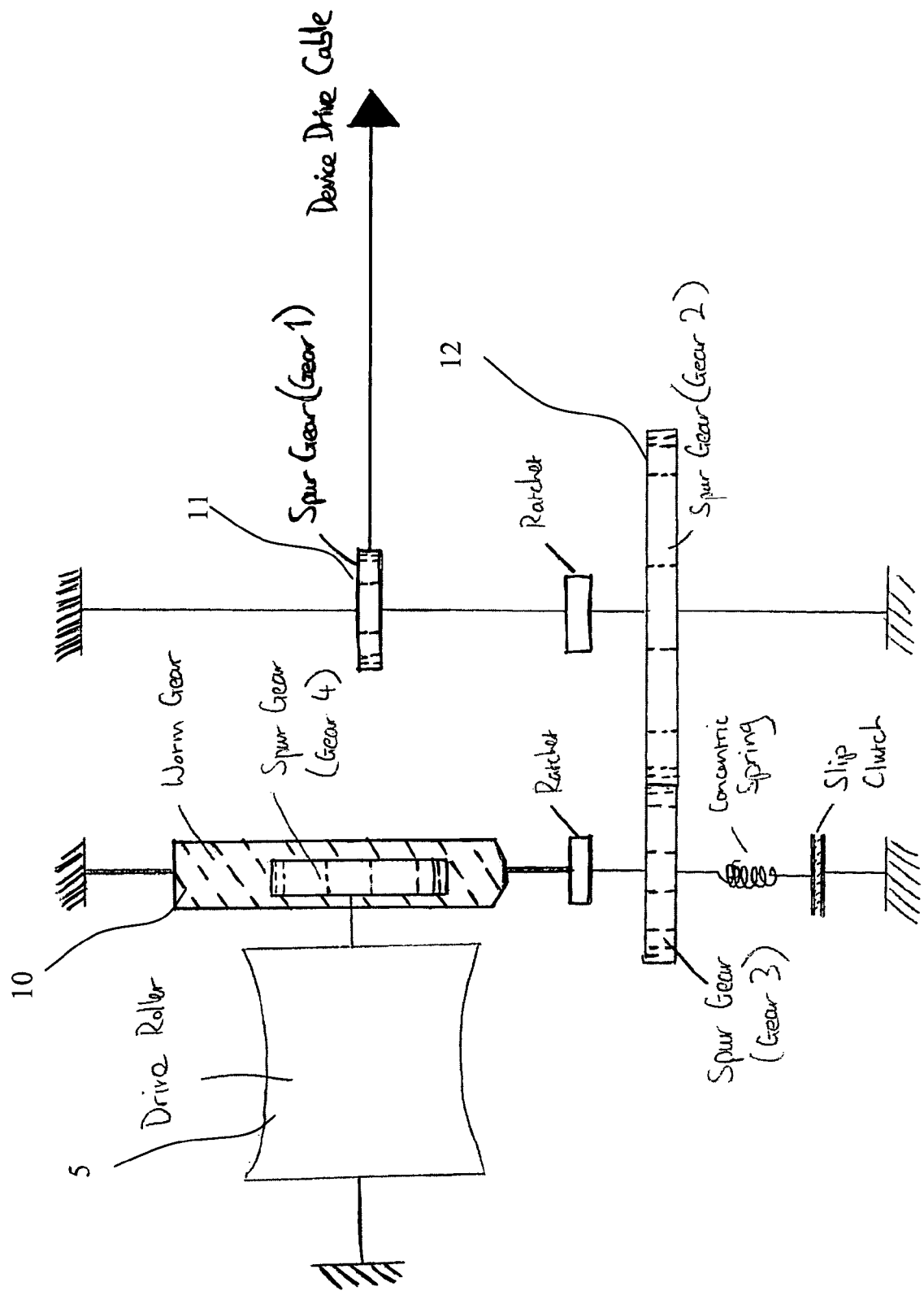
FIG. 5 illustrates a schematic illustrating the device gearbox: mechanical drive system.
Figure 6:
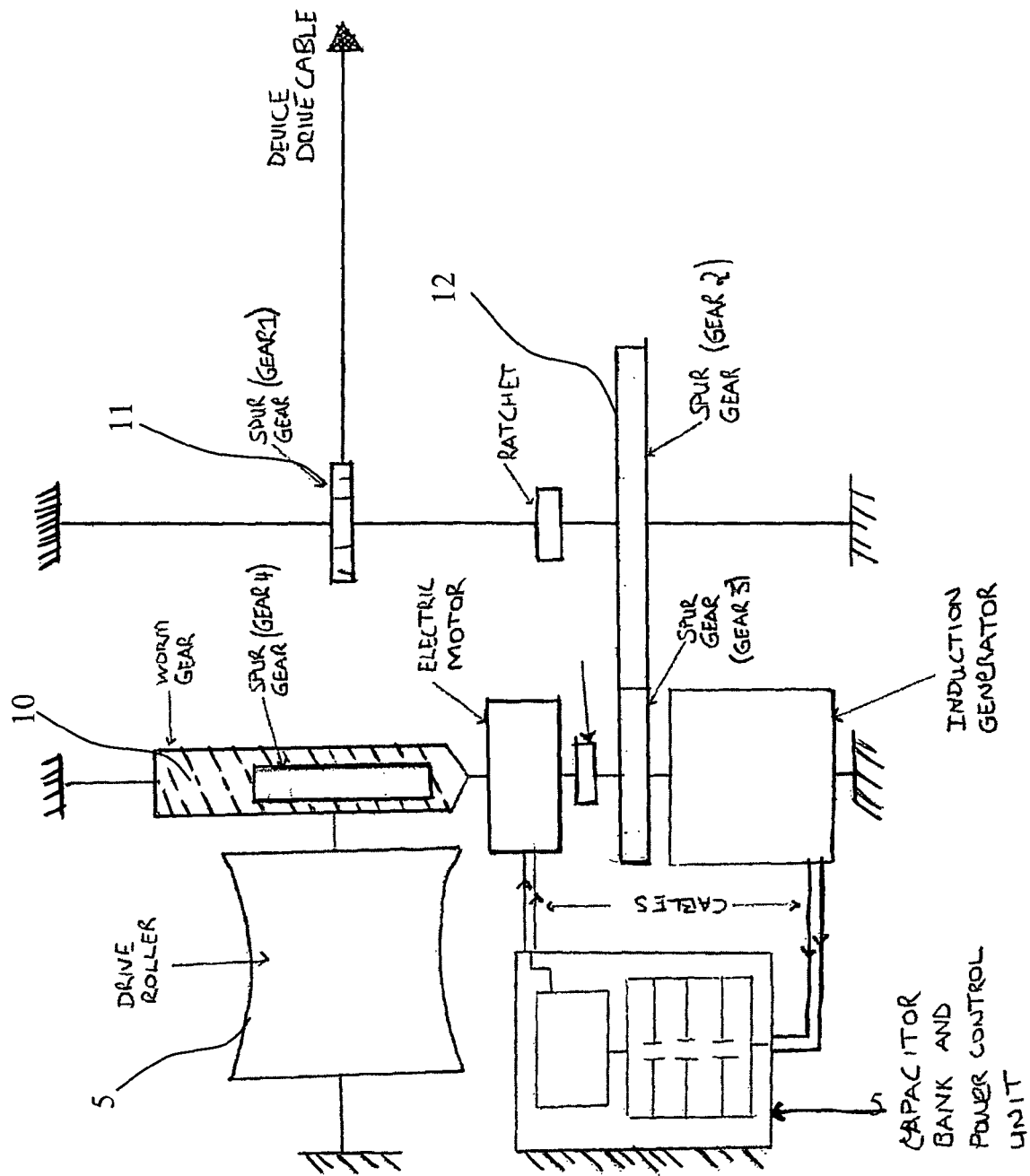
FIG. 6 illustrates a schematic illustrating the device gearbox: mechanical/electronic hybrid drive system.

Referring to FIGS. 5 and 6 the Door Handle/Pad Rotation Motor consists of a source of energy, a motor that converts the energy into a more useful form and a drive system to apply this transformed energy into door handle/pad rotation or drive, according to one aspect of the invention. The system utilises the kinetic energy from the opening of a door and uses this to power a machine that sterilises the door handle/pad once the user is no longer in contact with the device. It will be appreciated that in the context of the present invention door handle should be interpreted broadly and used to cover and type of device or mechanism that can be used to open a door.

The kinetic energy is harnessed by using the displacement that occurs between the inner edge of the door within the door jamb and the fixed door surround. This displacement is harnessed by attaching a non-elastic but flexible cord (e.g. a multi-link chain) between a fixed point in the fixed door surround within the door jamb, as illustrated in FIG. 1. This cord is connected to the motor within the device enclosure through a channel bored through the door. The linear displacement of this cord is converted into rotational displacement of a shaft. The cord is fixed to the shaft or preferably engages with a fixed gear cog (Gear 1) (11) mounted in the shaft, resulting in rotation of the shaft (Shaft 1). In parallel to Gear 1, a second Gear cog (Gear 2) (12) is fixed at another point along the shaft. The section of the shaft between Gear 1 and 2 is broken but connected using preferably a ratchet mechanism or any other device that allows independent movement or rotation of the shaft ends. Gear 2 can be different to Gear 1, in terms of diameter, material, number of teeth and/or any standard gear cog characteristic known to a person skilled in the art. Preferably, Gear 2 will be selected to increase the gearing of the overall system. This gearbox is represented as a schematic shown in FIG. 5.

A second shaft is located in parallel to Shaft 1. Shaft 1 and Shaft 2 mechanically engage with each other through the physical meshing of the teeth of Gear 2 with those of Gear 3. Gear 3 is a fixed gear cog on Shaft 2. The rotation of Shaft 2 as a result of the door being opened is converted into potential energy and stored using means known to a person skilled in the art. This potential energy is used to drive the door handle rotation motor and is preferably stored using a coil spring mechanism (FIG. 5), induction generator/electrical capacitor bank combination (FIG. 6) or any energy conversion/storage combination device known to one skilled in the art. The spring mechanism is located on one side of gear 3 and fixed to the fixed shaft mounting point. A slip clutch is located between the coil spring mechanism and the fixed shaft mounting point to ensure that the coil spring cannot be damaged by inappropriate use (excessive coiling/tightening of the mechanism) of the door sterilisation device. Preferably, the coil spring is pre-tensioned using a restrictive collar to ensure efficient and complete operation of the device.

Figure 7:
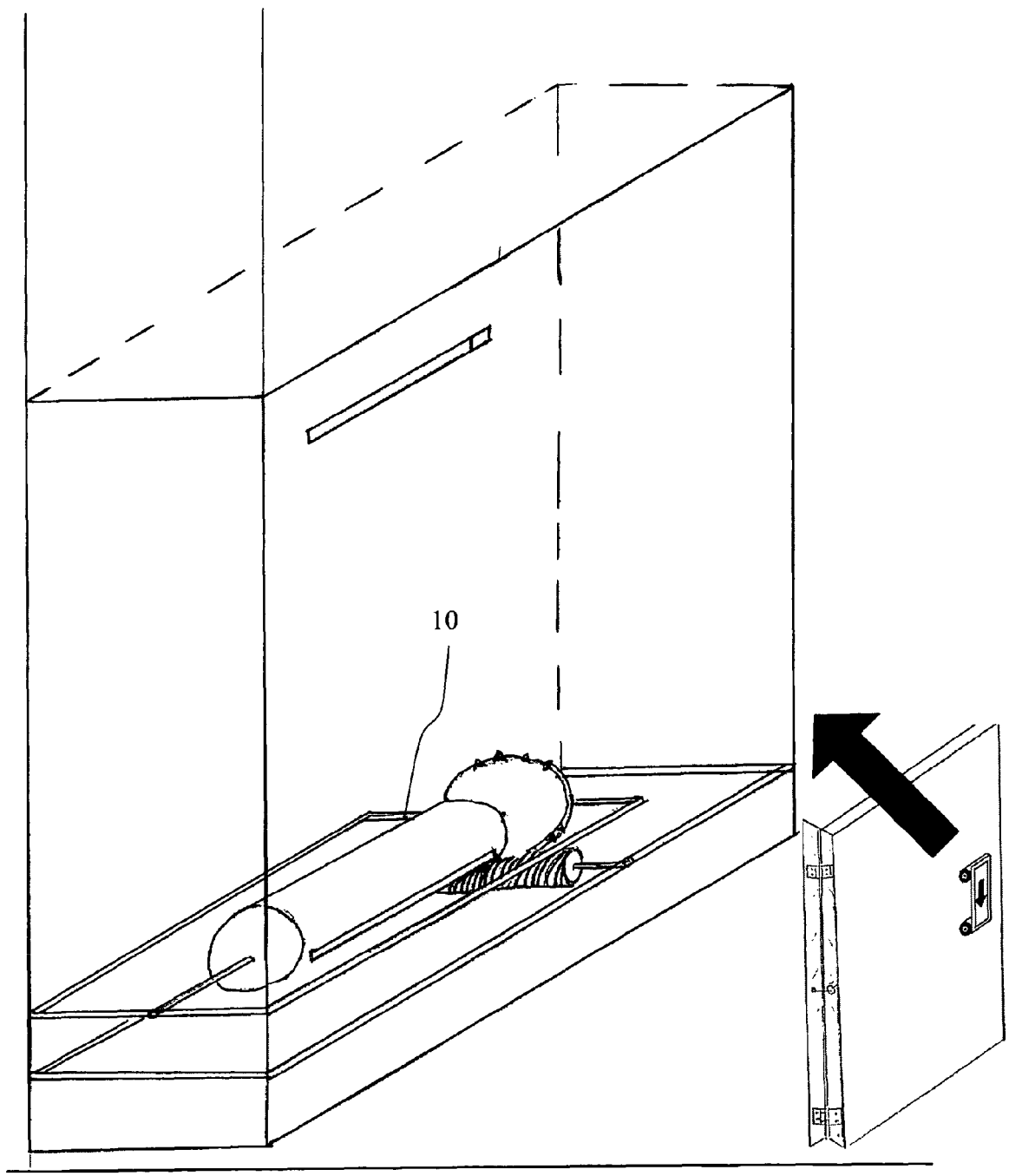

The section of the shaft on which gear three is fixed to a driving worm gear (10) is broken but connected using preferably a ratchet mechanism or any other device that allows independent movement or rotation of the shaft ends. This is to ensure that the device is not activated during the opening of the door, ensuring that the device is charged and will only operate once the door handle/pad is released and only when the door is closing. The worm gear (10) attached to shaft two rotates only when the door handle/pad is released and the door is closing. The worm gear teeth engage with a spur gear which is mounted coaxially with one of the driving roller mounting shafts. Consequently, when the worm gear rotates, one of the rollers rotates, driving the door handle (4) or alternatively the door pad material (7). The application of a worm (10) and spur gear (11, 12) drive train ensures that the door handle/pad cannot be moved/rotated by the user and the application of force/torque to the external interfaces. Device operation only occurs when the external interfaces are released. Conversely, the application of force or torque to the external interfaces will halt movement of the interfaces, ensuring safe and ergonomic operation of the device at all times. FIG. 7 illustrates a schematic of the worm gear drive mechanism in a door according to the invention, indicated by the reference numeral (10). It will be appreciated that other gear transmissions can be used to provide the means for rotating the door handle.

In another aspect of the invention the sterilisation machine can be in the form of a light source supplying UV light. As the door handle rotates the UV light is irradiated on the surface of the door handle killing any harmful microorganisms on the surface of the door handle.

Figure 8:
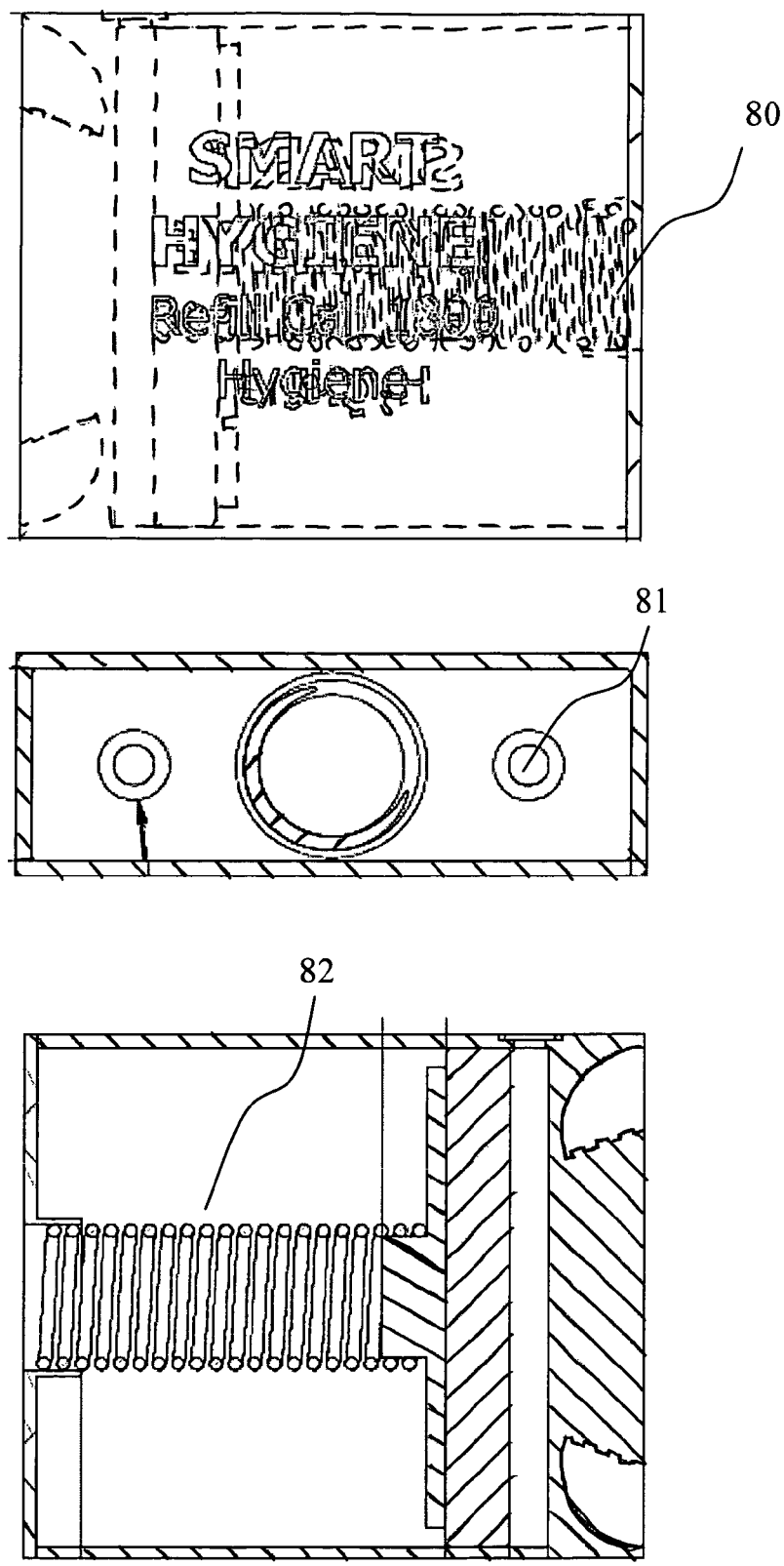
FIG. 8 shows a cartridge for storing disinfectant liquid to be used in conjunction with the drive/roller system, according to one aspect of the invention.
Figure 9:
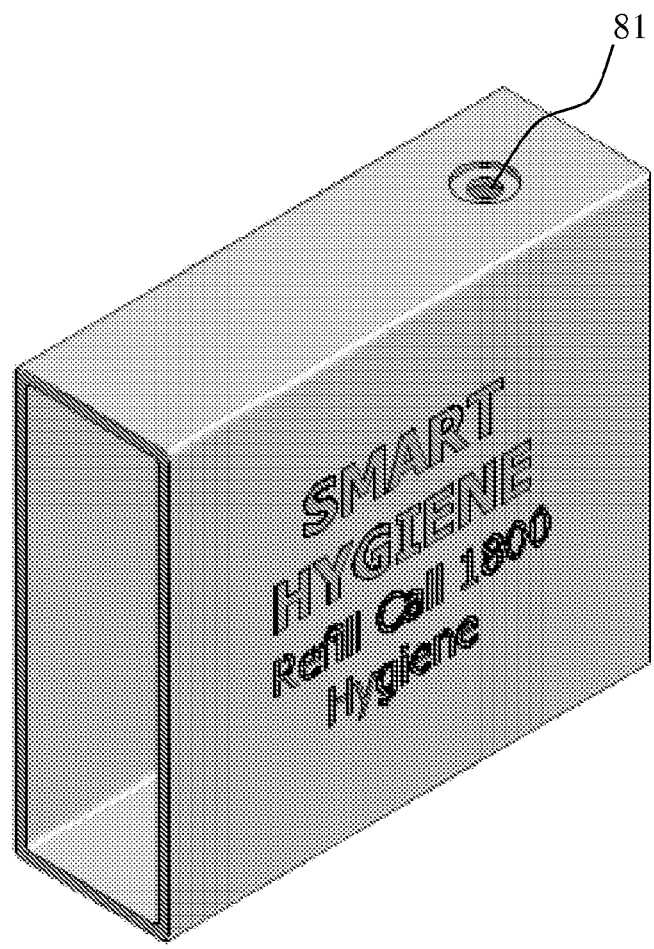
FIG. 9 is a 3D perspective view of the cartridge illustrated in FIG. 8.
Figure 10:
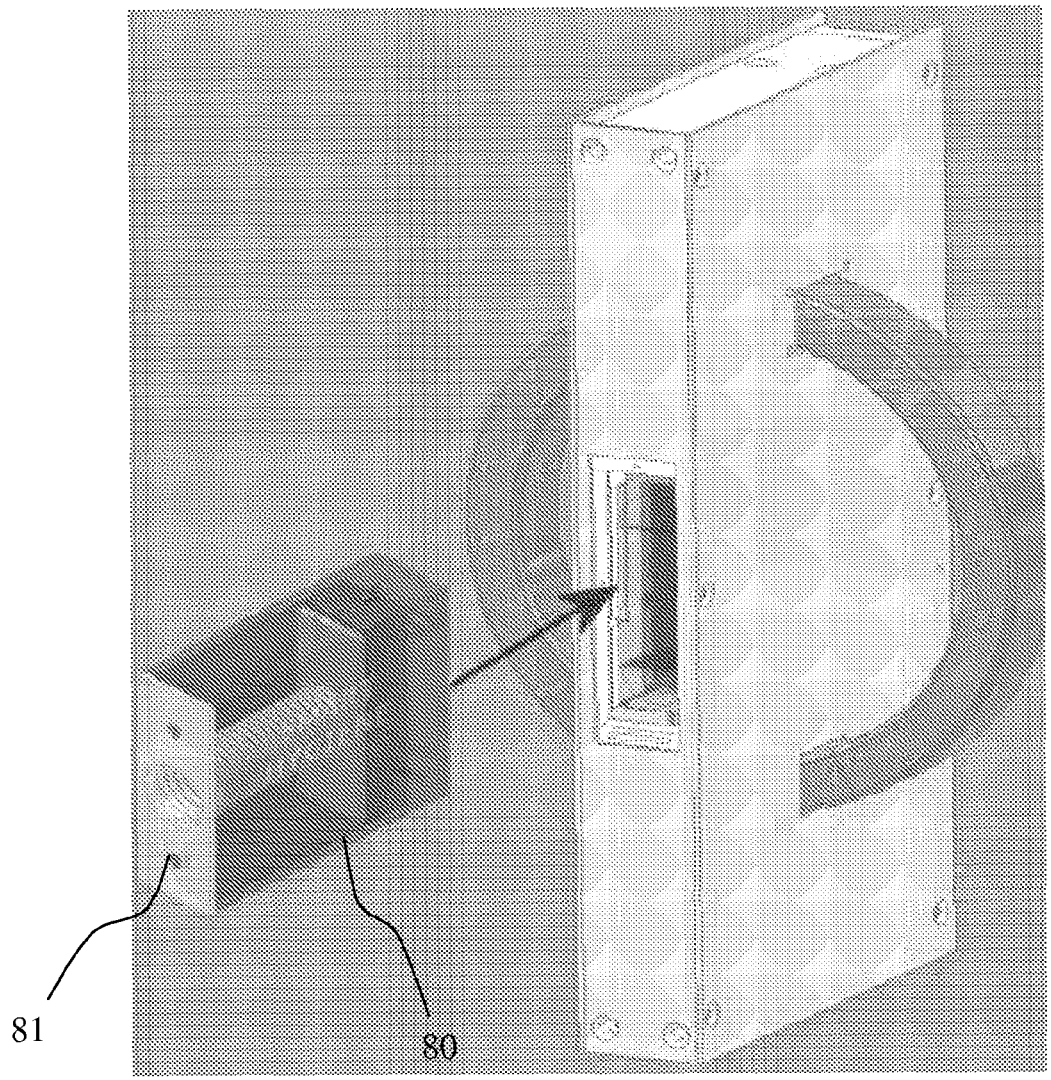
FIG. 10 illustrates how the cartridge is adapted to cooperate with drive roller to supply disinfectant liquid to clean said door handle.

In a further embodiment of the invention the disinfectant reservoir can be provided in the form of a disposable or refillable cartridge, as illustrated in FIGS. 8 to 10. FIG. 8 shows a cartridge for storing disinfectant liquid illustrated generally by the reference numeral 80. The cartridge (80) comprises a visible indicator (81) to indicate the amount of disinfectant liquid stored in said cartridge and ready for use. The cartridge comprises a spring based element (82) to apply a force on said liquid to ensure optimum supply of liquid to said drive roller. The spring based element (82) ensures that sufficient force is applied to the liquid such that a requisite supply of disinfectant is supplied to the rollers to ensure the door handle is cleaned properly.

FIG. 9 shows a 3D perspective view of the cartridge illustrated in FIG. 8 with the visible indicator (81).

FIG. 10 illustrates how the cartridge is adapted to cooperate with drive roller to supply disinfectant liquid to clean said door handle. The cartridge (80) can be easily slotted into the door panel and adapted such that the indicator (81) is visible to indicate when disinfectant liquid is running low or that the cartridge is empty. The cartridge can be replaced with a new disposable cartridge or simply refilled with disinfectant material as appropriate.

Figure 11:
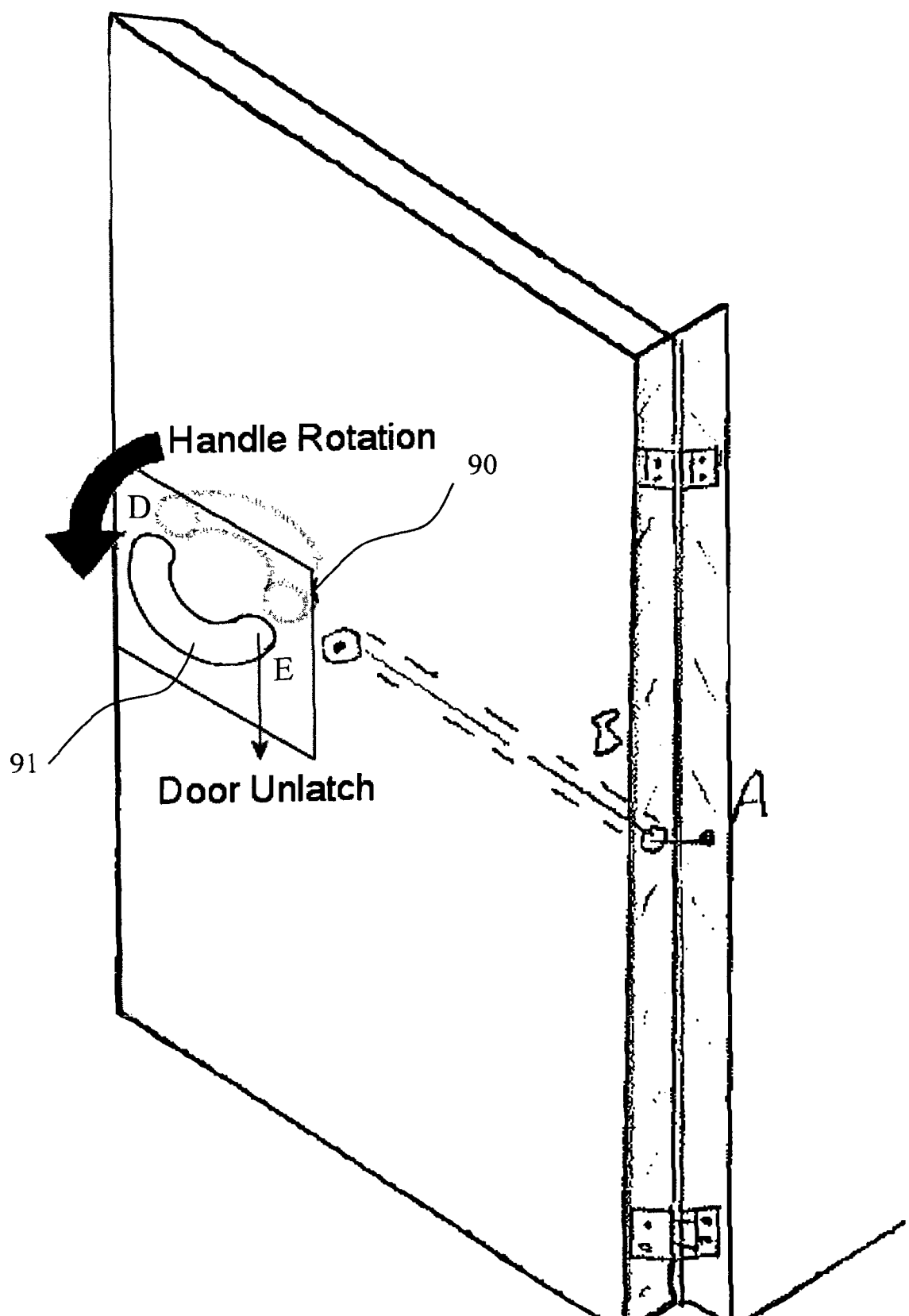
FIG. 11 illustrates a schematic illustrating the layout of the circular door handle orientated horizontally and the associated displacement according to another embodiment of the invention.
Figure 12:
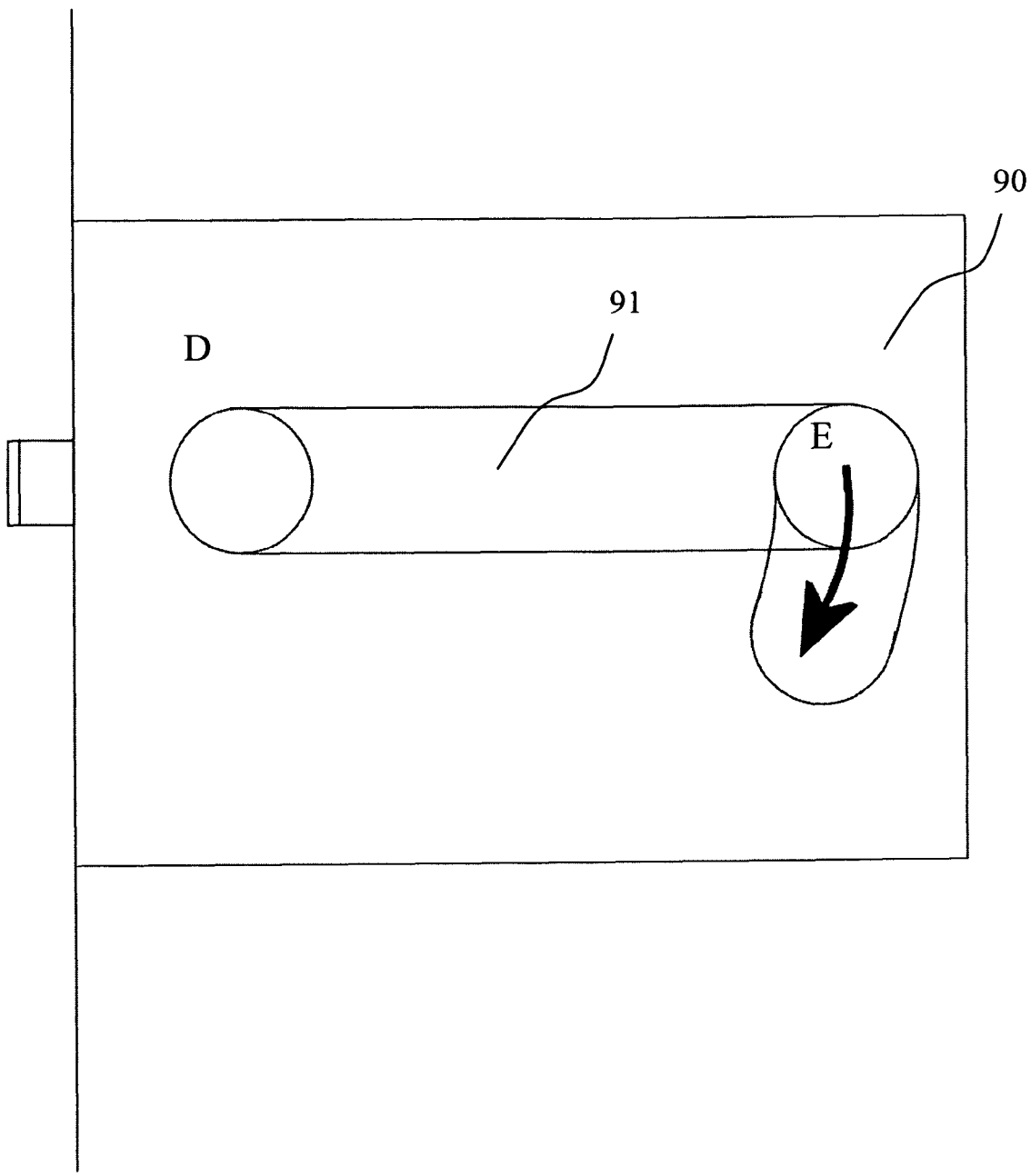
FIG. 12 illustrates a schematic illustrating an elevation view of the rotating handle orientated horizontally of the embodiment shown in FIG. 11.

FIGS. 11 and 12 illustrates a schematic illustrating the layout of a circular door handle orientated horizontally and the associated displacement used to power the rotating mechanism and operate an associated door latch mechanism, according to another embodiment of the invention and indicated generally by the reference numeral (90). In this embodiment a latched door handle (91) is shown, the handle orientation is rotated by 90 degrees, as described above, and the supporting and driving rollers are located within frames that can permit rotation and/or displacement about their geometric centres. The mechanism of sterilisation and handle rotation are identical to the previous embodiments, but the method of generating the required potential energy is different. The kinetic energy created by an individual applying downward pressure on the handle to open the latch is adapted to be harnessed to generate the required energy to rotate the handle as previously described. The stored potential energy is released as the handle is released by the user and returns to its original position and moves the handle through the 180 degrees as described in the previous embodiments. The handle (91) is fixed and pivoted at point D (FIG. 12) but is free to pivot or rotate to allow translation of point E. At point E, the handle mounting point can move down when a force is applied, with sufficient displacement to retract an integral door latching mechanism, allowing a closed latched door to be opened. Once the force is removed, the handle can return to its starting position, returning the latch to its starting position and allowing the door to be closed and latched, like any other door handle and latch mechanism.

While the invention has been described herein with reference to several especially preferred embodiments, these embodiments have been presented by way of example only, and not to limit the scope of the invention. Additional embodiments thereof will be obvious to those skilled in the art having the benefit of this detailed description, especially to meet specific requirements or conditions. Further modifications are also possible in alternative embodiments without departing from the inventive concept.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A system for self-cleaning a door handle by utilising the kinetic energy of opening a door, comprising:
   a cable comprising a multi-link chain fixed to a door frame and a transmission assembly such that linear displacement of said cable is converted to potential energy in response to movement of said door; and
   means for rotating a drive roller to co-operate with the door handle to rotate and to clean said door handle, only when the door handle is released and the door is closing,
   wherein the means for rotating comprises a worm, bevel or helical gear.

2. The system as claimed in claim 1 comprising a friction braking mechanism adapted to cooperate with said means for rotating such that when a user applies a force to the door handle the rotation of the handle stops; or
   wherein the means for rotating comprises a differential transmission; or
   wherein the means for rotating comprises a system of pulleys connected to an energy storing device, said energy storing device is adapted to store said potential energy; or
   wherein the means for rotating comprises a rack and pinion system connected to the energy storage device; or
   wherein the means for rotating comprises a system of clockwork style clutches and cams.

3. The system of claim 1 wherein the means for rotating comprises a worm, bevel or helical gear and wherein the means for rotating further comprises a spur, bevel or helical gear.

4. The system of claim 1 wherein the means for rotating comprises a worm, bevel or helical gear and wherein the means for rotating further comprises a spur, bevel or helical gear, and wherein the worm gear cooperates with a shaft, such that the shaft rotates only when the door handle is released and the door is closing.

5. The system of claim 1 wherein the means for rotating comprises a worm, bevel or helical gear and wherein the means for rotating further comprises a spur, bevel or helical gear, and wherein the worm gear cooperates with a shaft, such that the shaft rotates only when the door handle is released and the door is closing, and wherein the worm gear teeth engage with the spur gear and mounted coaxially with one of a driving roller mounting shaft to rotated said drive roller.

6. The system of claim 1 wherein the means for rotating comprises a worm, bevel or helical gear and wherein the means for rotating further comprises a spur, bevel or helical gear, and wherein the worm gear cooperates with a shaft, such that the shaft rotates only when the door handle is released and the door is closing, and wherein the worm gear teeth engage with the spur gear and mounted coaxially with one of a driving roller mounting shaft to rotated said drive roller; and wherein a ratchet mechanism coupled to the worm gear allows independent movement or rotation of the shaft ends, such that the ratchet mechanism only allows rotation in one direction.

7. The system of claim 1 wherein the cable is connected to the means for rotating and the door frame through a channel bored through the door; or wherein the cable is connected to the means for rotating and the door frame through a conduit positioned along the surface of the door.

8. The system of claim 1 wherein potential energy stored is used to rotate the door handle at least through 180 degrees of rotation.

9. The system of claim 1 wherein the potential energy generated is stored using a potential energy storage mechanism.

10. The system of claim 9 wherein the potential energy storage mechanism is a spring coil.

11. The system as claimed in claim 1 wherein an induction generator/electrical capacitor bank device combination is provided to convert the potential energy to stored electrical energy.

12. A system as claimed in claim 1 wherein an induction generator/electrical capacitor bank device combination is provided to convert the potential energy to stored electrical energy, the system comprising a differential transmission adapted to be used to dissipate the energy stored in the energy storage device.

13. The system as claimed claim 1 comprising a cartridge for storing disinfectant liquid.

14. The system as claimed in claim 1 comprising a cartridge for storing disinfectant liquid and wherein said cartridge cooperates with said drive roller to supply disinfectant liquid to clean said door handle.

15. The system as claimed in claim 1 comprising a cartridge for storing disinfectant liquid, wherein said cartridge cooperates with said drive roller to supply disinfectant liquid to clean said door handle, wherein said cartridge comprises a spring based element to apply a force on said liquid to ensure optimum supply of liquid to said drive roller, and wherein said cartridge comprises a visible indicator to indicate the amount of disinfectant liquid stored in said cartridge.

16. The system as claimed in claim 1 wherein the door handle is fixed in a horizontal orientation at a fixed mounting point at one end adapted to allow a relative amount of displacement at the opposite end, facilitating angular displacement of the handle about the fixed mounting point, wherein said angular displacement generates potential energy to facilitate rotation of the door handle to clean said handle.

17. A system for self-cleaning a door handle by utilising the kinetic energy of opening a door, comprising:
   a cable comprising a multi-link chain fixed to a door frame and a transmission assembly such that linear displacement of said cable is converted to potential energy in response to movement of said door; and
   means for rotating a drive roller to co-operate with the door handle to rotate and to clean said door handle, only when the door handle is released and the door is closing,
   wherein a required quantity of potential energy for the means for rotation is generated after said door opens through an angle of 30 degrees or greater about the door rotational axis with respect to the door frame.

18. A system for self-cleaning a door handle by utilising the kinetic energy of opening a door, comprising:
   a cable comprising a multi-link chain fixed to a door frame and a transmission assembly such that linear displacement of said cable is converted to potential energy in response to movement of said door; and
   means for rotating a drive roller to co-operate with the door handle to rotate and to clean said door handle, only when the door handle is released and the door is closing,
   wherein the potential energy generated is stored using a potential energy storage mechanism in the form of a spring coil mechanism, and wherein a slip clutch is located between the coil spring mechanism and a fixed shaft mounting point to ensure that the coil spring to prevent excessive coiling/tightening of the coil spring mechanism.

19. The system of claim 18 wherein the coil spring is pre-tensioned using a restrictive collar to ensure efficient and complete operation of the system.

20. A system for self-cleaning a door handle by utilising the kinetic energy of opening a door, comprising:
   a cable comprising a multi-link chain fixed to a door frame and a transmission assembly such that linear displacement of said cable is converted to potential energy in response to movement of said door;
   means for rotating a drive roller to co-operate with the door handle to rotate and to clean said door handle, only when the door handle is released and the door is closing, and
   a cartridge for storing disinfectant liquid, wherein said cartridge cooperates with said drive roller to supply disinfectant liquid to clean said door handle and wherein said cartridge comprises a spring based element to apply a force on said liquid to ensure optimum supply of liquid to said drive roller.

* * * * *